United States Patent [19]

Collins

[11] 4,040,418
[45] Aug. 9, 1977

[54] SURGICAL DRAPE WITH RETAINING MEANS

[75] Inventor: Robert F. Collins, Barrington, Ill.

[73] Assignee: The Kendall Company, Boston, Mass.

[21] Appl. No.: 676,029

[22] Filed: Apr. 12, 1976

[51] Int. Cl.² .............................................. A61B 19/06
[52] U.S. Cl. ................................................ 128/132 D
[58] Field of Search ................. 128/132 D, DIG. 26, 128/292, 275, 155

[56] References Cited

U.S. PATENT DOCUMENTS

| | | | |
|---|---|---|---|
| 3,435,821 | 4/1969 | Bennett | 128/132 D |
| 3,856,006 | 12/1974 | Krzewinski | 128/132 D |

*Primary Examiner*—Lawrence W. Trapp
*Attorney, Agent, or Firm*—Powell L. Sprunger

[57] ABSTRACT

A surgical drape for use in association with auxiliary equipment, such as a tube or cord. The drape has sheet means of a material resistant to passage of bacteria and a fenestration for placement over a surgical site. The drape also has tie means secured to the drape for retaining the equipment at a fixed location on the drape as related to the patient.

13 Claims, 8 Drawing Figures

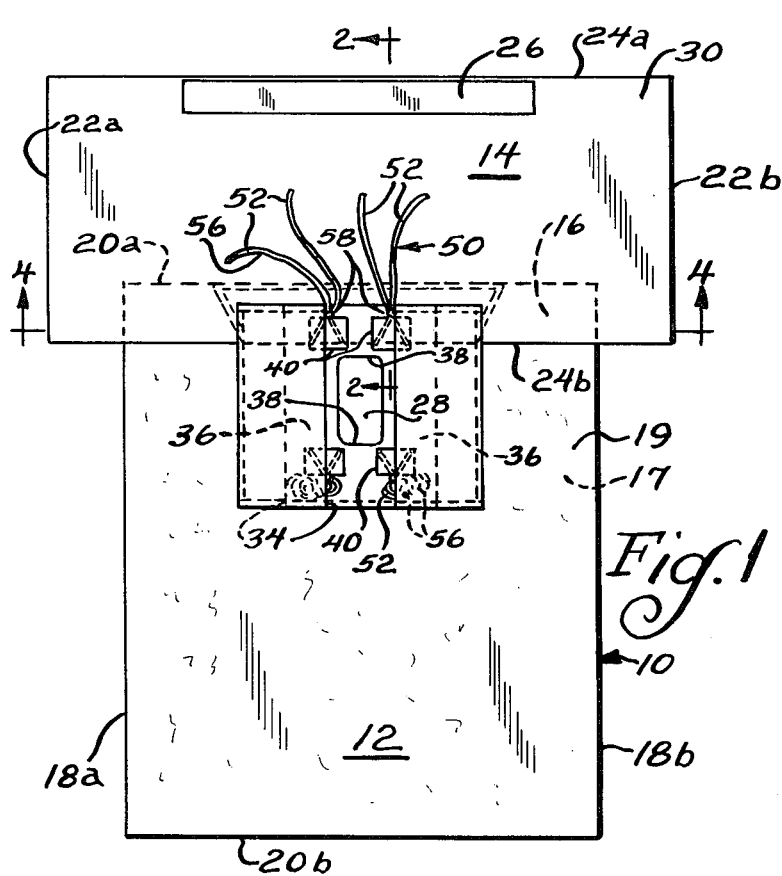
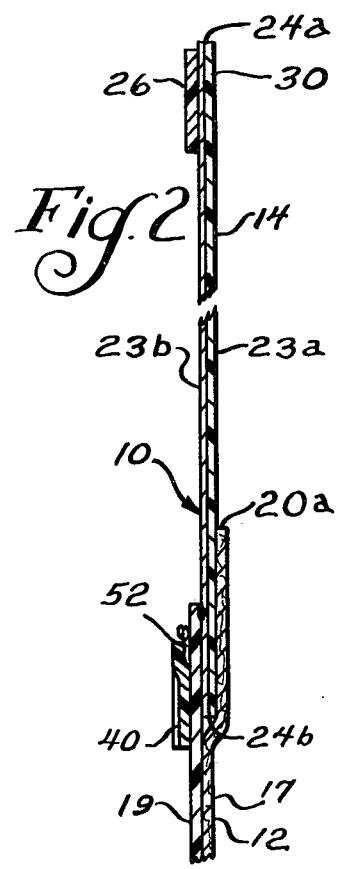
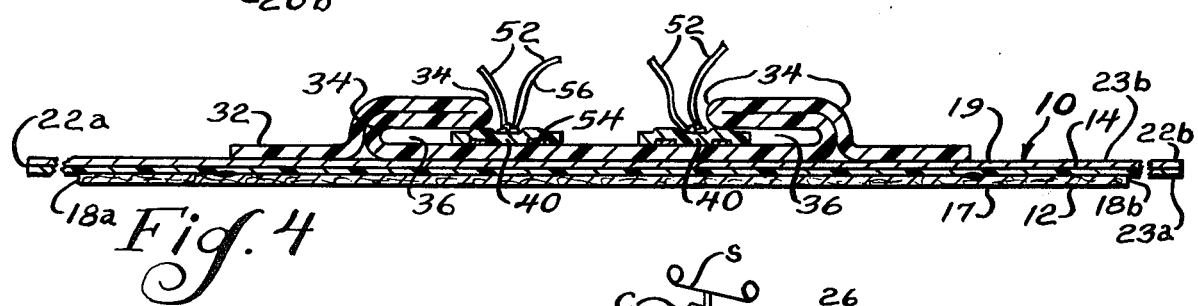
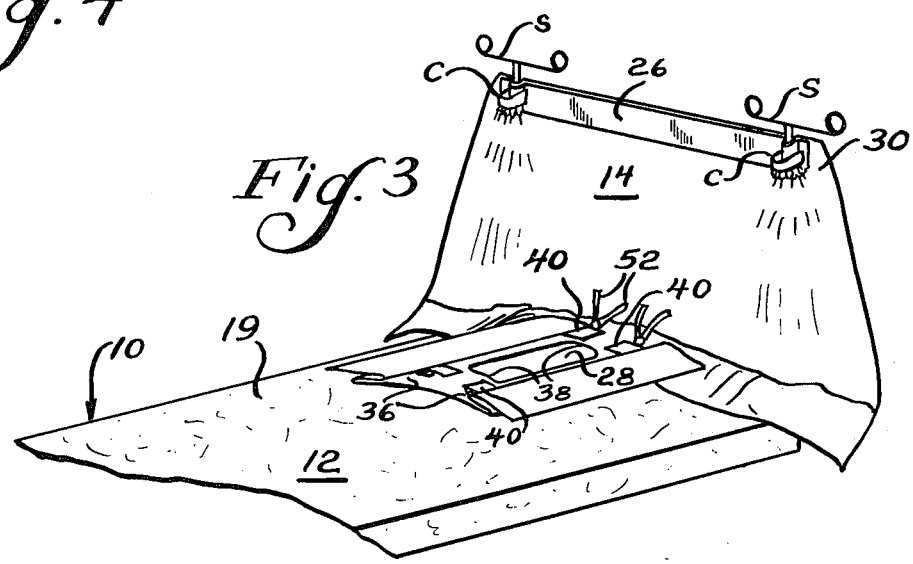

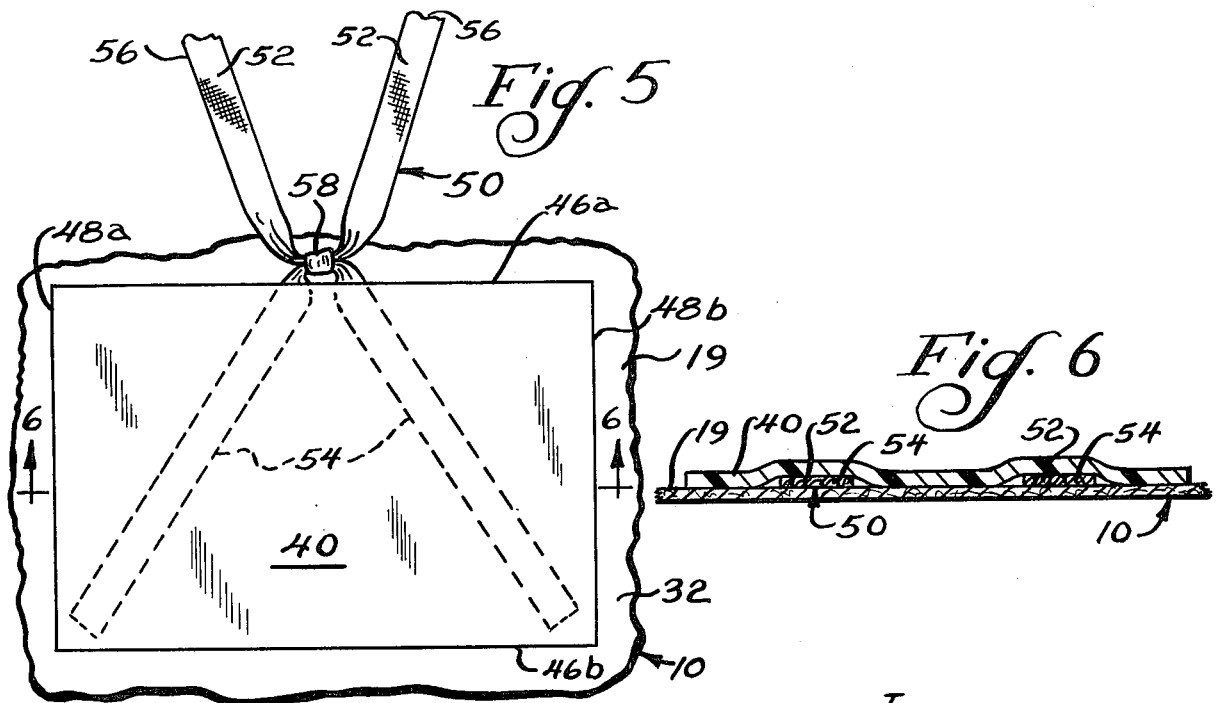
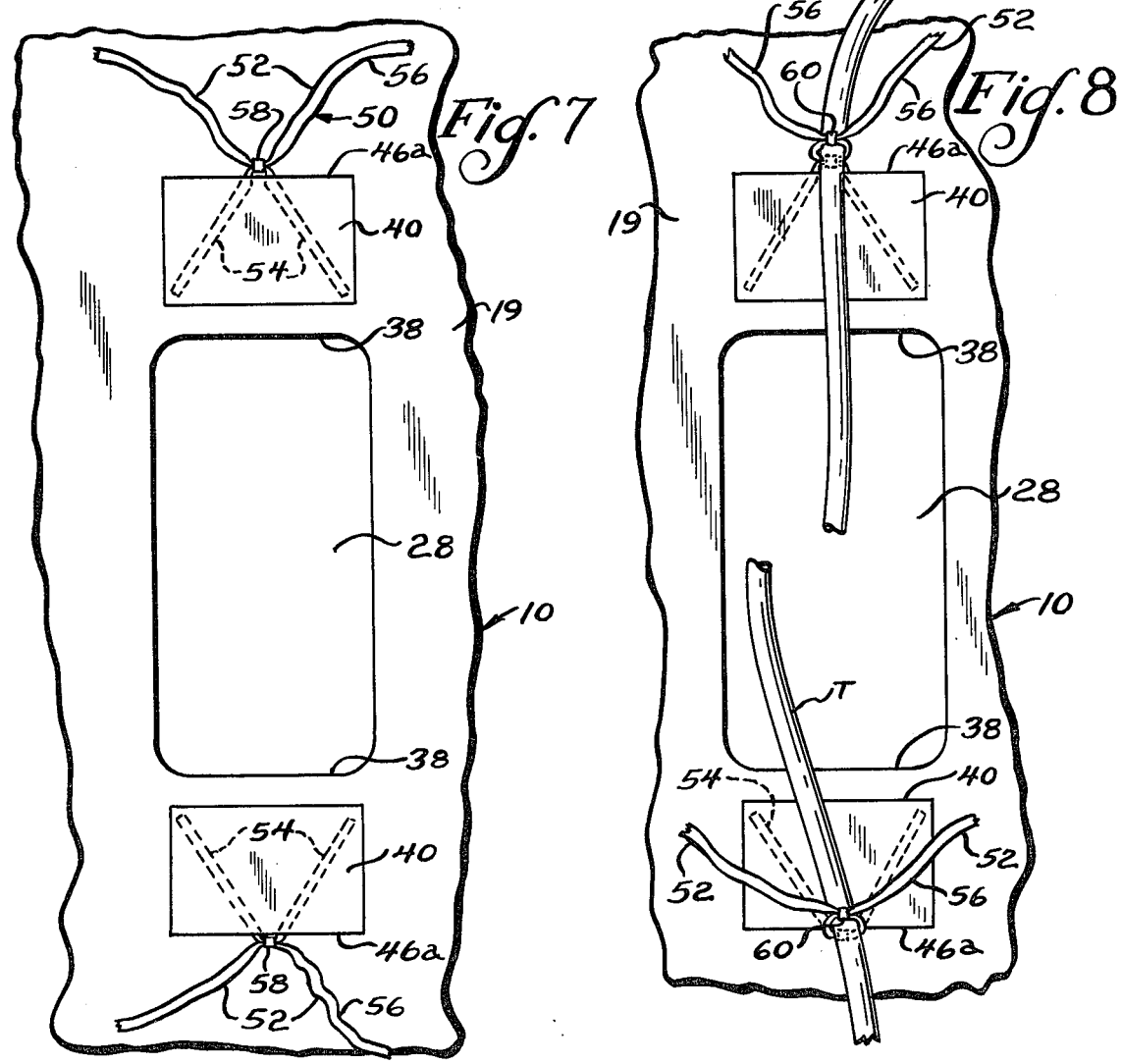

SURGICAL DRAPE WITH RETAINING MEANS

BACKGROUND OF THE INVENTION

The present invention relates to disposable articles, and more particularly to surgical drapes.

An assortment of disposable drapes have been proposed for use during surgical procedures and operations. Such drapes normally have sheet with a fenestration for placement over the surgical site. During certain operations, e.g., open heart surgery, tubes and other equipment of a similar nature may pass over the drape to the surgical site. Examples of such equipment include tubing for a heart-lung machine, aspiration tubing, fibrillator cord, defibrillator cord, pacing cord, etc. Of course, it is necessary to secure such tubes or cords in place on the drape to prevent them from moving relative the surgical site and from obstructing the surgeon during the operation.

If clips are attached directly to the drape, they may puncture the drape and destroy the sterile barrier required over the patient, a procedure sometimes practiced. Hence, certain surgeons place loose linens over the drape and use clips to attach the equipment to the linens. However, this procedure is inconvenient and time-consuming, and the linens do not totally prevent movement of the equipment.

The prior drapes have also suffered in other respects. Certain of the drapes, e.g., disposable cardiovascular drapes, have end portions attached to retaining stands, e.g., i.v. stands, adjacent the patient's head, but the drapes have frequently torn from the attachment clips. Also, some surgeons have found it necessary to additionally place linens over the end portion of the drape adjacent the patient's head, since the disposable drapes were deemed an inadequate sterile barrier and of insufficient strength between the surgical site and the patient's head, anesthesiologist, or observers.

SUMMARY OF THE INVENTION

A principal feature of the present invention is the provision of a surgical drape which permits securement of auxiliary equipment to the drape in a sure and simplified manner.

The drape of the present invention comprises, sheet means of a material resistant to passage of bacteria having a pair of side edges, and a fenestration intermediate the side edges. The drape has a pair of ties secured to the drape adjacent the fenestration and having free ends extending from the drape. The drape also has a sheet of durable material adjacent one end of the drape located adjacent the patient's head when the drape is placed, and a sheet of fluid impervious material covering at least a portion of the drape in a region between the fenestration and the one end of the drape.

A feature of the present invention is that the ties may be used to retain the auxiliary equipment, such as a tube or cord, on the drape in a simplified manner.

Another feature of the invention is that the ties retain the equipment on the drape without destroying the sterile barrier provided by the drape.

Yet another feature of the invention is that the ties firmly retain the equipment at a fixed location relative the fenestration and surgical site.

Still another feature of the invention is that the sheet of durable material of adequate strength permits securement of the one drape end to stands, such as i.v. stands, by clips without tearing the drape.

Another feature of the invention is that the fluid impervious sheet provides a complete sterile barrier between the surgical site and the patient's head.

Further features will become more fully apparent in the following description of the embodiments of this invention and from the appended claims.

DESCRIPTION OF THE DRAWINGS

In the drawings:

FIG. 1 is a plan view of a surgical drape of the present invention;

FIG. 2 is a fragmentary sectional view taken substantially as indicated along the line 2—2 of FIG. 1;

FIG. 3 is a fragmentary perspective view of the drape of FIG. 1 as positioned for a surgical operation;

FIG. 4 is a fragmentary sectional view taken substantially as indicated along the line 4—4 of FIG. 1;

FIG. 5 is a fragmentary view taken on an enlarged scale of an anchor sheet and ties for the drape of FIG. 1;

FIG. 6 is a fragmentary sectional view taken substantially as indicated along the line 6—6 of FIG. 5;

FIG. 7 is a fragmentary view of another embodiment of the drape of the present invention; and FIG. 8 is a fragmentary plan view of the drape of FIG. 7 showing tubing as attached by ties on the drape.

DESCRIPTION OF THE PREFERRED EMBODIMENTS

Referring now to FIG. 1, there is shown a surgical drape generally designated 10 having a main sheet 12, and a wing sheet 14 attached by suitable means, such as adhesive, to an end portion 16 of the main sheet 12. The drape 10 may be utilized for any suitable surgical procedure or operation, although the drape is particularly useful for open heart surgery. The main sheet 12 has a pair of side edges 18a and 18b, and a pair of end edges 20a and 20b connecting the side edges 18a and b. The wing sheet 14 also has a pair of side edges 22a and 22b, and a pair of end edges 24a and 24b connecting the side edges 22a and b. As shown, side portions of the wing sheet 14 adjacent the side edges 22a and b extend past the side edges 18a and b of the main sheet 12. The drape 10 has an inner surface 17 facing toward the patient after placement of the drape, an outer surface 19 facing away from the patient in the placed drape, and a fenestration 28 in the main sheet 12 located intermediate the side edges 18a and b.

In a preferred form, the main sheet 12 may be made of a fluid repellent material, such as a treated nonwoven material, while the wing sheet 14 comprises a laminate of an inner fluid impervious sheet 23a and an outer fluid repellent sheet 23b, such as a laminate of polyethylene and a nonwoven material. As shown in FIGS. 1–3, the wing sheet 14 has an elongated slip sheet or panel 26 of durable material, such as Tyvek, a trademark of E. I. du Pont de Nemours. The clip panel 26 is attached by any suitable means, such as by adhesive, to the wing sheet 14 adjacent the end edge 24a of the wing sheet 14, and the clip panel 26 extends laterally along a substantial central portion of the end edge 24a, as shown.

With reference to FIG. 3, the drape 10 is placed over the patient such that the fenestration 28 is located over the surgical site. An end portion 30 of the wing sheet 14 is then attached in the region of the clip panel 26 by means of clips C to a vertical stand S, such as an i.v. stand. In the usual configuration, two stands S are located adjacent the patient's shoulders on opposed sides of the patient's head, such that the attached wing sheet 14 assumes a generally vertical configuration in front of the patient's head. Thus, the fluid impervious sheet 23a of the wing sheet 14 provides a sufficient sterile barrier between the fenestration 28 or surgical site and the patient's head, the anesthesiologist, or observers, thus eliminating the necessity of placing linens over this portion of the drape. Also, the clip panel 26 prevents tearing of the wing sheet 14 by the clips C while attached to the stands S, thus minimizing the possibility that the wing sheet 14 may fall from the stands and destroy the sterile barrier in front of the patient's head.

Referring to FIGS. 1 and 4, the drape 10 may have a reinforcement sheet 32 secured to the outer surface of the main sheet 12 and having a plurality of longitudinally extending fold lines 34, with edge portions of the folded sheet 32 being secured by adhesive to the main sheet 12, and with side portions of the doubled reinforcement sheet defined by fold lines 34 being attached by adhesive to the underlying portion of the reinforcement sheet, such that pockets 36 are defined facing toward the fenestration 28. During the operation, body fluids, such as blood, pass from the surgical site through the fenestration 28 into the pockets 36 where the fluids are retained, thus preventing passage of the fluids onto the floor and the surgeon's gown.

Referring to FIGS. 1-6, the drape 10 has a plurality of anchor sheets 40 attached to the reinforcement sheet 32 or drape 10 by suitable means, such as adhesive. As shown, the anchor sheets 40 are secured to the drape at a location adjacent opposed ends 38 of the elongated fenestration 28, although it will be understood that the anchor sheets may be secured to the drape at any suitable location for use in retaining auxiliary equipment, as will be described below. With reference to FIGS. 5 and 6, the anchor sheets 40 have a pair of side edges 46a and 46b, and a pair of end edges 48a and 48b connecting the side edges 46a and 46b. As desired, the anchor sheets 40 may have any suitable shape in addition to the rectangular shape shown.

As best shown in FIGS. 5 and 6, the drape has tie means 50 comprising a pair or set of ties 52. Each of the ties has a first end portion 54 secured between the anchor sheet 40 and the underlying drape or sheet, and a second free end portion 56 extending from the retaining sheet 40 at the side edge 46a remote the fenestration. Also, the ties 52 have a knot 58 adjacent the side edge 46a of the anchor sheet 40. As shown, the first end portions 54 of the ties are widely spaced from each other beneath the anchor sheet 40, and extend from the side edge 46a toward the juncture of the side edge 46b and the end edges 48a and b. Thus, when forces are applied to the free end portions 56 of the ties 52, the knot 58 assures that stress on the attached portions 54 of the ties beneath the anchor sheet will be normally applied in shear rather than peel, and the spaced tie end portions 54 cause distribution of the forces beneath the anchor sheet 40. Accordingly, the secured end portions 54 of the ties 52 may be subjected to a substantial amount of force before the anchor sheet 40 or the ties will pull from the drape. Additionally, with reference to FIG. 1, it will be seen that the knots 58 of the ties 52 are located at sides of the anchor sheets remote the fenestration 28, such that normal forces which are applied to the ties will be directed away from the anchor sheets and fenestration 28, thus adding to the effective strength of the tie bonds during use of the drape. For example, cotton ties having a width of 7/16 inch have provided a strength permitting 35 to 40 lbs. pull before breakage.

As shown in FIG. 1, the drape 10 may have a pair of laterally spaced anchor sheets 40 and associated sets of ties 52 adjacent each of the opposed fenestration ends 38, with the ties being located adjacent the pockets 36 of the drape. In this configuration, the multiple ties 52 provide a number of uses, and the tie end portions 56 may be readily stored in the pockets 36 of the drape prior to use, or during the operation if unused at this time. Thus, the pockets 36 provide a convenient sterile storage location for the tie end portions 56 in order to remove them from the region around the fenestration when not in use. With reference to FIGS. 7 and 8, in an alternative form, a single anchor sheet 40 and associated ties 52 may be located adjacent both opposed ends 38 of the fenestration 28. Also, any number of anchor sheets 40 and associated ties 52 may be located around the fenestration 28 or at other desired location on the drape for purposes which will be described below. As before, the knots 58 in the ties 52 are located adjacent the side edge 46a of the anchor sheets 40, in order that forces are normally applied to the tie ends 54 in a direction away from the anchor sheets.

After the drape has been positioned over the patient and the wing sheet 14 has been attached to the stands S by the clips C, auxiliary equipment, such as tubes or cords, may be placed at the desired position on the drape leading to the fenestration or surrounding areas. Examples of such equipment which may be used during a cardiovascular procedure include tubing for a heart-lung machine, aspiration tubing, fibrillator cord, defibrillator cord, and other miscellaneous tubes and cords. With reference to FIG. 8, after the drape has been secured to the patient, the ties are utilized to retain the equipment, such as tubes T, at the desired position adjacent the fenestration by tying the free tie end portions 56 around the tubes T into a knot 60. In this manner, the tubes T and other equipment are securely retained at a fixed position where certain of the equipment may pass through the fenestration 28 into the surgical site during the operation. Also, the equipment is secured by the ties in a simple manner, the ties 52 prevent significant movement of the equipment during the operation, and the ties 52 permit securement of the equipment to the drape without loss of the sterile barrier provided by the drape 10. In certain instances, it may be desirable to permit some movement of the equipment relative the drape, and the equipment may be tied by the ties at a location spaced from the knots 58, or the knots 58 may be spaced a distance from the anchor sheets 40.

The foregoing detailed description is given for clearness of understanding only, and no unnecessary limitations should be understood therefrom, as modifications will be obvious to those skilled in the art.

I claim:

1. A surgical drape for use in association with auxiliary equipment, such as a tube or cord, comprising:
   sheet means of a material resistant to passage of bacteria and having a fenestration for placement over a surgical site; and
   tie means secured to the drape and spaced from a side of the fenestration for retaining said equipment at a fixed location on the drape.

2. The drape of claim 1 wherein the tie means comprises, first and second tie sets located adjacent opposed ends of said fenestration.

3. The drape of claim 1 wherein the tie means comprises, a pair of laterally spaced tie sets located adjacent an end of the fenestration.

4. The drape of claim 3 wherein the tie means comprises, a second pair of laterally spaced tie sets located adjacent an opposed end of the fenestration.

5. A surgical drape for use in association with auxiliary equipment, such as a tube or cord, comprising:
   sheet means of a material resistant to passage of bacteria having a pair of side edges and a fenestration intermediate said side edges; and
   tie means secured to the drape adjacent to and spaced from a side of said fenestration, said tie means comprising a pair of associated tie ends extending from the drape for retaining said equipment at a fixed location adjacent the fenestration.

6. The drape of claim 5 including an anchor sheet secured to the drape, and in which the tie ends include portions secured beneath the anchor sheet.

7. The drape of claim 6 wherein the tie ends extend from an edge of the anchor sheet remote the fenestration.

8. The drape of claim 6 wherein the tie ends include a knot adjacent an edge of the anchor sheet.

9. The drape of claim 5 wherein said drape includes a sheet defining a pocket intermediate the fenestration and at least one side edge, and in which said tie means is located sufficiently close to said pocket for placement of the tie ends therein.

10. A surgical drape for use in association with auxiliary equipment, such as a tube or cord, comprising:
    sheet means of a material resistant to passage of bacteria and having a fenestration for placement over a surgical site;
    an anchor sheet secured to the drape adjacent the fenestration; and
    a pair of ties having a pair of spaced ends secured beneath said anchor sheet, a first pair of spaced ends secured beneath said anchor sheet, a knot retaining said ties together adjacent an edge of the anchor sheet remote the fenestration, and a second pair of free ends for securing said equipment to the drape.

11. A surgical drape, comprising:
    a main sheet having a pair of side edges; and
    a wing sheet extending from an end of the main sheet, said wing sheet having a pair of sides extending past both side edges of the main sheet, and including a fluid impervious sheet extending substantially throughout the wing sheet and providing a barrier to prevent passage of bacteria therethrough.

12. A surgical drape comprising:
    a main sheet of a material resistant to passage of bacteria; and
    a wing sheet extending from an end of the main sheet and having an end edge remote the main sheet, said wing sheet having sheet means of a durable material adjacent said end edge to prevent tearing of the wing sheet when retained by clips.

13. The drape of claim 12 wherein said sheet means comprises a panel of durable material extending along a substantial portion of said end edge.

* * * * *

UNITED STATES PATENT AND TRADEMARK OFFICE
CERTIFICATE OF CORRECTION

PATENT NO. : 4,040,418
DATED : August 9, 1977
INVENTOR(S) : Robert F. Collins

It is certified that error appears in the above-identified patent and that said Letters Patent are hereby corrected as shown below:

Column 1, line 9, after "have" insert -- a -- .

Column 1, line 10, after "certain" insert -- of the --.

Column 2, line 55, "slip" should be -- clip -- .

Column 6, line 6, delete "pair of spaced ends secured"

Column 6, line 7, delete "beneath said anchor sheet, a.".

Signed and Sealed this

Twenty-ninth Day of November 1977

[SEAL]

Attest:

RUTH C. MASON
*Attesting Officer*

LUTRELLE F. PARKER
*Acting Commissioner of Patents and Trademarks*